US00PP26013P2

(12) United States Plant Patent
Morgan

(10) Patent No.: US PP26,013 P2
(45) Date of Patent: Oct. 20, 2015

(54) ***GENTIANA* PLANT NAMED 'LITTLE PINKIE'**

(50) Latin Name: *Gentiana hybrida*
Varietal Denomination: Little Pinkie

(71) Applicant: Edmond Robert Morgan, Palmerston North (NZ)

(72) Inventor: Edmond Robert Morgan, Palmerston North (NZ)

(73) Assignees: THE NEW ZEALAND INSTITUTE FOR PLANT AND FOOD RESEARCH LTD., Aukland (NZ); John Maffat, Tuatapere (NZ)

( * ) Notice: Subject to any disclaimer, the term of this patent is extended or adjusted under 35 U.S.C. 154(b) by 76 days.

(21) Appl. No.: 13/999,510

(22) Filed: Mar. 5, 2014

(51) Int. Cl.
*A01H 5/00* (2006.01)

(52) U.S. Cl.
USPC ..... Plt./433

(58) Field of Classification Search
USPC ..... Plt./433
See application file for complete search history.

*Primary Examiner* — Susan McCormick Ewoldt
(74) *Attorney, Agent, or Firm* — Penny J. Aguirre

(57) ABSTRACT

A new cultivar of *Gentiana* plant named 'Little Pinkie' that is characterized by its upright, clumping plant habit, its abundant blooms and long flowering period; blooming from May to October in the Netherlands and its flowers that are a distinct purple-pink color even when the flowers are closed.

2 Drawing Sheets

Botanical classification: *Gentiana hybrida.*
Varietal denomination: 'Little Pinkie'.

BACKGROUND OF THE INVENTION

The present invention relates to a new and distinct cultivar of *Gentiana* of interspecific hybrid origin in which *Gentiana scabra* is one of the known species in the background of the parentage. 'Little Pinkie' represents a new Gentian, an herbaceous perennial grown for landscape use.

The new cultivar was derived from a controlled breeding program by the Inventor in Aukland, New Zealand. The Inventor made a cross between an unnamed proprietary plants in the Inventor's breeding program, reference no. 5W65 as the female parent and reference no. Pink A as the male parent. The Inventor selected 'Little Pinkie' as a single unique plant in February of 2008 amongst the seedlings that resulted from the above cross.

Asexual propagation of the new cultivar was first accomplished under the direction of the Inventor by in vitro propagation Aukland, New Zealand in April of 2008. Asexual propagation by stem cuttings and tissue culture has been determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Little Pinkie' as a new and unique cultivar of *Gentiana.*

1. 'Little Pinkie' exhibits an upright, clumping plant habit.
2. 'Little Pinkie' exhibits abundant blooms and a long flowering period; blooming from May to October in the Netherlands.
3. 'Little Pinkie' exhibits flowers that are a distinct purple-pink color even when the flowers close.

The female parent of 'Little Pinkie', ref no. 5W65, differs from 'Little Pinkie' in having red flowers. The male parent of 'Little Pinkie', ref no. Pink A., differs from 'Little Pinkie' in having flowers that are more pink in color and borne on longer stems. 'Little Pinkie' can be most closely compared to the *Gentiana scabra* cultivar 'Zuki Rindo' (not patented). 'Zuki Rindo' is similar to 'Little Pinkie' in blooming late in the season. 'Zuki Rindo' differs from 'Little Pinkie' in blooming later in the fall, in having smaller flowers that are more grey-pink in color when they are closing, in having 50% less flowers, in having thinner stems, and in having a more spreading, groundcover-like plant habit.

BRIEF DESCRIPTION OF THE DRAWINGS

The accompanying colored photographs illustrate the overall appearance and distinct characteristics of the new *Gentiana*. The photographs were taken of plants 12 months in age as grown in a half open greenhouse in a 2-liter container in Boskoop, The Netherlands.

The photograph in FIG. 1 provides a side view of the plant habit of 'Little Pinkie'.

Figure 1:
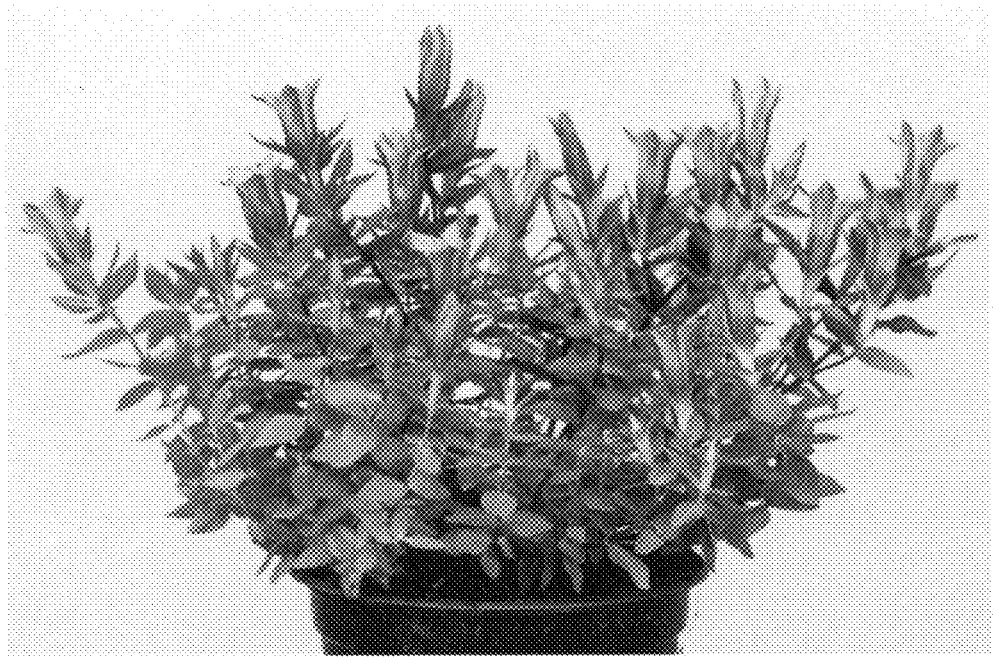
Figure 2:
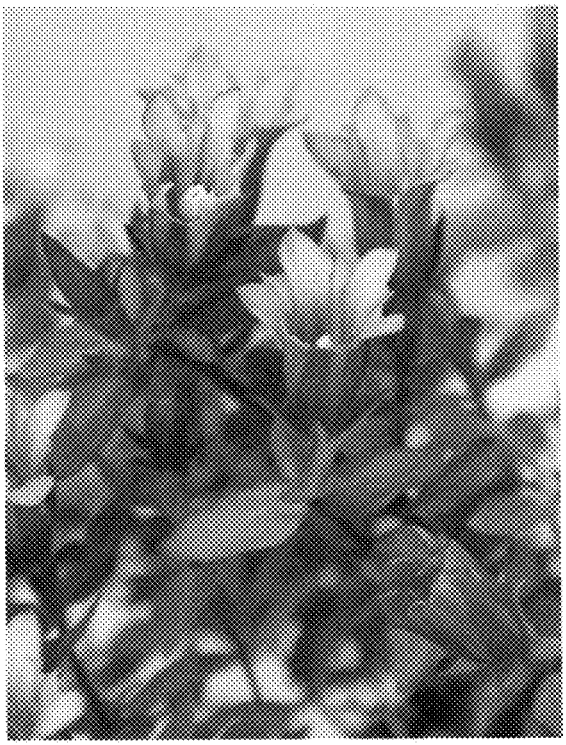

The photograph in FIG. 2 provides a close-up view of the flowers of 'Little Pinkie'.

Figure 3:
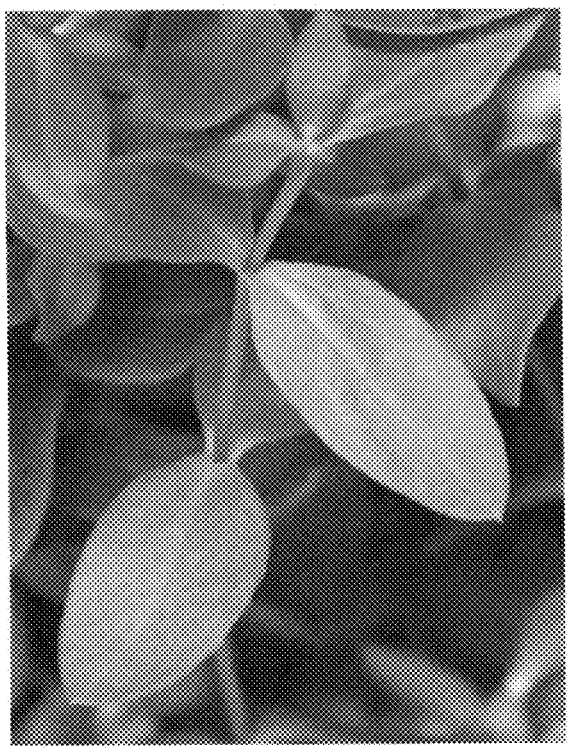

The photograph in FIG. 3 provides a close-up view of the foliage of 'Little Pinkie'.

The colors in the photographs are as close as possible with the photographic and printing technology utilized and the color values cited in the detailed botanical description accurately describe the colors of the new *Gentiana.*

DETAILED BOTANICAL DESCRIPTION OF THE PLANT

The following is a detailed description of 12 month-old plants as grown in a half open greenhouse in two-liter containers in Boskoop, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Continuously from May to October in The Netherlands.

*Plant type* .—Herbaceous perennial.

*Plant habit*.—Upright, clump-forming.

*Height and spread*.—An average of 23 cm in height and 38 cm in spread.

*Cold hardiness*.—Hardy to at least U.S.D.A. Zone 6.

*Diseases and pests*.—No unique susceptibility or resistance to diseases or pests known has been observed.

*Root description*.—Fine and fibrous.

*Propogation type*.—In vitro propagation and stem cuttings.

*Growth rate*.—Moderate.

Stem description:

*Stem shape*.—Rounded.

*Stem color*.—A blend of N186C and 145C.

*Stem size*.—Main stems; an average of 16.6 cm in length and 3 mm in diameter, lateral stems; an average of 4.8 cm in length and 2 mm in diameter.

*Stem surface*.—Slightly glossy, glabrous, scabridulous.

*Stem aspect*.—Main stems held primarily upright with lateral stems held at an average angle of 35° to the main stems.

*Internode length*.—An average of 1.6 cm.

*Branching habit*.—Basal branching with an average of 29 main stems and 3 lateral branches per main stem.

Foliage description:

*Leaf shape*.—Ovate.

*Leaf division*.—Simple.

*Leaf base*.—Attenuate.

*Leaf apex*.—Acute.

*Leaf venation*.—Pinnate, color; upper surface 144C and lower surface 144C to 144D.

*Leaf margins*.—Entire.

*Leaf attachment*.—Sessile.

*Leaf arrangement*.—Opposite.

*Leaf surface*.—Upper and lower surface; slightly coriacious, upper surface; dull, lower surface; slightly glossy.

*Leaf color*.—Immature leaves upper surface 143A to 143B and lower surface 145A, Mature leaves upper surface 143A and lower surface 144C.

*Leaf number*.—An average of 22 (11 pairs) per main stem and 6 (3 pairs) per lateral branch.

*Leaf size*.—An average of 2.9 cm in length and 1.7 cm in width.

Flower description:

*Flower type*.—Terminal, solitary, tubular flowers.

*Flower fragrance*.—None.

*Flower lastingness*.—An average of 10 days on plant, persistent.

*Flower bud description*.—Narrowly elliptic shape, an average of 1.5 cm in diameter (including sepals), 0.6 cm in length (excluding sepals) and 3.6 mm in length, color; petal portion is N77B with the apex N78A and calyx portion is 145B to 145C with the tips of the immature sepals 143A.

*Flower quantity*.—An average of 1 per stem.

*Flower aspect*.—Held upright.

*Flower shape*.—Tubular with the lower 86.5% fused.

*Flower size*.—An average of 5.0 cm in depth and 2.7 cm in diameter.

*Peduncles*.—An average of 2 mm in length and 1 mm in width, held upright relative to stem, strong, 145C in color.

*Pedicel*.—Not present.

*Petal description*.—5, oblong in shape, 86.5% of lower portion is fused into a tubular shape, margin; mostly fused with free parts serrate, apex is broadly acute, both surfaces glabrous, upper surface is slightly glossy, lower surface is glossy.

*Petal size*.—An average of 5.2 cm in length and 9 mm in width.

*Petal color*.—Opening and fully open upper surface; N74C, tube N77C suffused with 198D and base 145C to 145D, opening lower surface; N74C, tube N77B and base 145C to 145D, fully open lower surface N78A to N78B, tube N77B to N77C suffused with 198D and base 145C to 145D.

*Calyx form*.—Campanulate and rotate.

*Calyx size*.—An average of 3.0 cm in length and 2.6 cm in diameter.

*Sepal description*.—An average of 5, oblanceolate in shape, margin is entire, apex is narrowly acute, base is cuneate with the lower 55% fused, both upper and lower surfaces are glabrous, upper surface is dull and lower surface is slightly glossy.

*Sepal size*.—An average of 3.0 cm in length, 5 mm in width.

*Sepal color*.—Immature upper surface; basal half 145D, apical half 143A, immature lower surface; basal half 144C suffused with N77D and apical half 143B, mature upper surface; basal half 145D and apical half 141A, mature lower surface; basal half 144B and apical half a blend of 143B and 144A.

Reproductive organs:

*Gynoecium*.—1 Pistil, an average of 4 mm in length, stigma is pointed in shape and 157B in color, style is an average 3 mm in length and 157B in color, ovary is 145B in color.

*Androecium*.—5 stamens, anthers are oblong in shape, basifixed, an average of 3 mm in length and 4A in color, filaments are an average of 3.3 cm in length and a blend between 150D and 157A in color, pollen is moderately abundant and 2C in color.

*Fruit and seed*.—No fruit or seed has been observed.

It is claimed:

1. A new and distinct cultivar of *Gentiana* plant named 'Little Pinkie' as herein illustrated and described.

* * * * *